United States Patent

Reynolds, Jr.

Patent Number: 6,015,417
Date of Patent: *Jan. 18, 2000

[54] SURGICAL FASTENER

[76] Inventor: Walker Reynolds, Jr., 14 Rendalia Dr., Anniston, Ala. 36201

[*] Notice: This patent issued on a continued prosecution application filed under 37 CFR 1.53(d), and is subject to the twenty year patent term provisions of 35 U.S.C. 154(a)(2).

[21] Appl. No.: 08/909,746

[22] Filed: Aug. 12, 1997

Related U.S. Application Data

[63] Continuation-in-part of application No. 08/591,337, Jan. 25, 1996, abandoned.

[51] Int. Cl.⁷ .................................................. A61B 17/00
[52] U.S. Cl. .......................................................... 606/151
[58] Field of Search .................................... 606/151, 143, 606/157, 158, 219, 220, 221; 24/556, 545–546; 227/902

[56] References Cited

U.S. PATENT DOCUMENTS

| | | |
|---|---|---|
| 4,188,953 | 2/1980 | Klieman et al. . |
| 4,407,286 | 10/1983 | Noiles et al. . |
| 4,414,721 | 11/1983 | Hufnagel . |
| 4,489,875 | 12/1984 | Crawford et al. . |
| 4,512,345 | 4/1985 | Green . |
| 4,534,350 | 8/1985 | Golden et al. .......................... 606/220 |
| 4,671,276 | 6/1987 | Reynolds ............................ 606/219 X |
| 4,932,960 | 6/1990 | Green et al. . |
| 5,171,250 | 12/1992 | Yoon . |
| 5,201,746 | 4/1993 | Shichman . |
| 5,258,009 | 11/1993 | Conners ................................... 606/219 |
| 5,282,829 | 2/1994 | Hermes ................................... 606/219 |
| 5,352,229 | 10/1994 | Goble et al. .............................. 606/72 |
| 5,425,740 | 6/1995 | Hutchinson, Jr. ....................... 606/221 |
| 5,487,746 | 1/1996 | Yu et al. . |
| 5,509,920 | 4/1996 | Phillips et al. . |

Primary Examiner—Michael Buiz
Assistant Examiner—Vikki Trinh
Attorney, Agent, or Firm—Kenneth M. Bush; Veal & Bush, LLC

[57] ABSTRACT

An improved surgical fastener of the type used in a surgical applicator which has been modified to enhance the gripping capability of the fastener once secured. The fastener can have apertures therethrough or the surface can be knurled, crimped, etched with a laser, layered with an abrasive coating, sand blasted, punched, notched, or modified in any other manner which enhances the grip of the fastener when secured. Additionally, the fastener can be formed from or coated with a magnetic material, which provides additional holding power to maintain the clip closed after it has been secured into the tissue. An alternate embodiment includes a double wall to reinforce the fastener when secured.

7 Claims, 4 Drawing Sheets

SURGICAL FASTENER

RELATED PATENTS

This application is a continuation-in-part of U.S. patent application Ser. No. 08/591,337, filed Jan. 25, 1996, now abandoned.

FIELD OF THE INVENTION

The present invention relates to surgical fasteners. More particularly, the present invention relates to improved surgical fasteners of the type which are secured by surgical applicators. In even greater particularity, the present invention relates to improvements in surgical staples and clips.

BACKGROUND OF THE INVENTION

Surgical fasteners, including clips and staples, and methods of applying these fasteners are well known in the art. Surgical fasteners can be used to close incisions or wounds, or to clamp vessels or ducts to prevent fluid flow. Surgical applicators used to apply these fasteners comprise various designs depending on the use to which the fasteners are employed. For example, a clip applicator is typically a pistol-shaped vise used where a vessel or duct must be sealed. The clip is directed to the location of application and then the vise secures the clip, collapsing and sealing the vessel. A surgical stapler is typically used where an incision or wound must be closed. A surgical stapler typically employs an anvil to form the fastener during application. With increasing use and improvement of various surgical applicators, fasteners have also improved. Some examples of surgical fasteners are found in U.S. Pat. Nos. 4,407,286; 4,489,875; and 4,932,960.

In the '286 patent, Noiles et al. disclose a surgical staple which is designed to reduce the tendency of the staple to slip off the anvil during application or to adhere to the anvil after application. In the '875 patent, Crawford et al. disclose a self-centering staple to remedy the problem of misalignment of the staple during application. In the '960 patent, Green et al. disclose a bioabsorbable fastener designed for elastic expansion to prevent breakage. Although the foregoing surgical fasteners, as well as others known in the art, have addressed and remedied many problems encountered with the use of these fasteners, there still exist problems accompanying their use.

One such problem is the slippage of fasteners at the point of their application in the tissue. During surgery it is frequently required to shut off fluid transfer to areas, thus fasteners are often placed around blood vessels or other structures to achieve this. For example, in cases where polyps are to be removed, fasteners are typically applied to the base of the structure to shut off fluid transfer and the polyp is removed. The fastener is left in place during the healing process to prevent fluid loss. As hydrostatic pressure increases due to the blockage, fasteners tend to slip away from the pressurized area which can result in fastener displacement and fluid loss or hemorrhage. Another problem seen with currently used fasteners concerns the closure of the fastener itself. During application of the fastener, the typical U or V-shaped designs often result in non-uniform closure of the fastener over the vessel, which again can lead to fastener displacement as well as fluid loss or hemorrhage. To avoid these problems, the fastener is tightly fastened into the tissue encompassed by the fastener, which still does not guarantee against slippage. In addition, in surgeries where fasteners are employed to temporarily shut off blood flow through a vessel, this form of application can cause irreparable injury to the vessel.

From the foregoing it may be seen that a need exists for an improved surgical fastener which is designed to resist displacement once secured to the tissue.

SUMMARY OF THE PRESENT INVENTION

It is the object of the present invention to provide an improved surgical fastener of the type used in surgical applicators which resists displacement once secured to the tissue.

It is another object of the present invention to provide a fastener which can be used in surgical applicators presently available.

These and other objects of the present invention are accomplished through the use of a surgical fastener which has been modified to enhance the gripping capability of the fastener once secured. The fastener can have apertures therethrough or the surface can be knurled, crimped, etched with a laser, layered with an abrasive coating, sand blasted, punched, notched, or modified in any other manner which enhances the grip of the fastener when secured. Additionally, the fastener can be formed from or coated with a magnetic material, which provides additional holding power to maintain the clip closed after it has been secured into the tissue. For purposes of this disclosure, a knurled surface refers to a surface which has been roughened to provide an enhanced grip. Examples of knurling include serrations, dimples, protrusions, cross-hatches, grooves, and flutes pressed into a surface. The abrasive coating is a material such as non-toxic paint containing a plurality of solid particles wherein these particles form protrusions in the coating once applied to the fastener. The modification can be continuous over the entire surface of the fastener or it can be only on the tissue contacting surface, and can additionally have modified regions intermixed with unmodified regions. During the application of the fastener to the target tissue, the tissue conforms to the modified surface of the fastener. This results in resistance to slippage because the fastener surface presses into the tissue causing depressions in the tissue. Subsequently, tissue edema and growth encapsulates and integrates into deformities in the fastener. An alternate embodiment includes a double wall to reinforce the fastener when secured.

These and other objects and advantages of the invention will become apparent from the following detailed description of the preferred embodiment of the invention.

BRIEF DESCRIPTION OF THE DRAWINGS

A surgical fastener embodying features of my invention is described in the accompanying drawings which form a portion of this disclosure and wherein.

DETAILED DESCRIPTION OF THE PREFERRED EMBODIMENT

Figure 1:
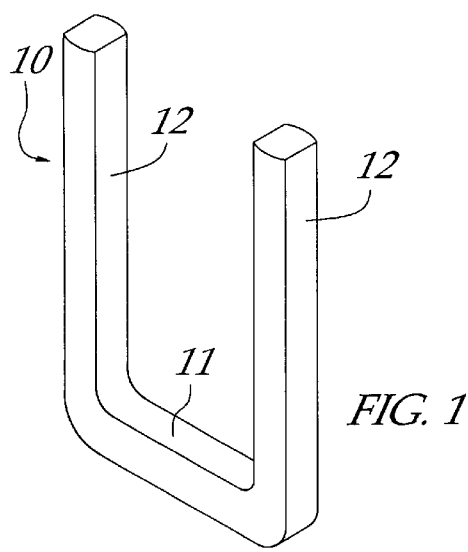
FIG. 1 is a perspective view of a square-cornered U-shaped fastener before application.
Figure 18:
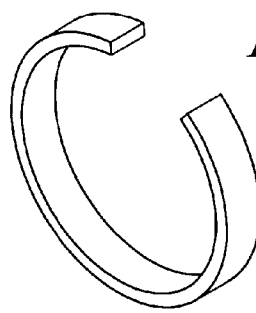
FIG. 18 is a perspective view of an alternate embodiment showing a C-shaped fastener before application.
Figure 15:
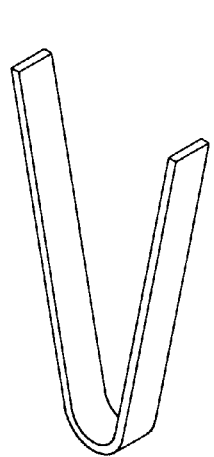
FIG. 15 is a perspective view of an alternate embodiment showing a V-shaped fastener before application.
Figure 16:
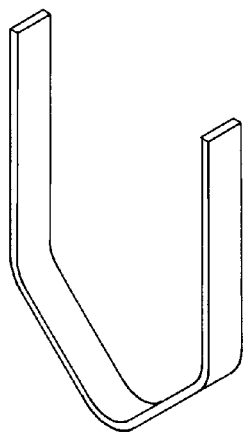
FIG. 16 is a perspective view of an alternate embodiment showing an alternate U-shaped fastener before application.
Figure 17:
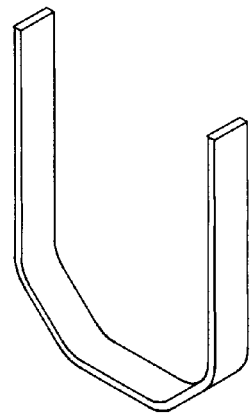
FIG. 17 is a perspective view of an alternate embodiment showing an alternate U-shaped fastener before application.

A more complete understanding of the invention may be obtained by reference to the accompanying drawings wherein the fastener, according to the embodiment illustrated in FIG. 1, is a square-cornered U-shaped member 10 having a base 11 and at least two parallel legs 12. The preferred embodiment is composed of titanium or stainless steel, although other metals, plastics, or ceramics can be used, as well as malleable wire. The preferred embodiment has a square cross-section, although the cross-section can be round or have any polygonal shape. Other embodiments of the present invention include a linear shaped member shown in FIG. 14, a V-shaped member shown in FIG. 15, other U-shaped members shown in FIG. 16 and FIG. 17, or a C-shaped member shown in FIG. 18. Another beneficial feature is a novel double wall, which acts to reinforce the fastener when secured. Embodiments of the present invention illustrating the double wall feature are shown in FIGS. 19–22, discussed in further detail hereinbelow. The embodiment of choice can depend on the personal preference of the user as well as the procedures for which the fasteners are to be used.

Typically, fasteners embodying features of my invention are formed from a sheet, or wire, of titanium or stainless steel which has been modified with a texturizing feature. Moreover, the fasteners can be formed from or coated with a magnetic material, which provides additional holding power to maintain the clip closed after it has been secured into the tissue. The sheets or wires are pulled from preformed rolls having a thickness usually between 0.015 to 0.025 inches. As the sheet or wire is pulled from the roll, it is pulled though a device for texturizing the sheet or wire. This texturizing device can be a crimping mechanism for crimping the sheet or wire; a knurling mechanism for pressing serrations, dimples, protrusions, cross-hatches, grooves, or flutes into the surface of the sheet or wire; an applicator for applying a non-toxic abrasive coating containing a plurality of solid particles to the surface of the sheet or wire; a series of lasers for etching into, or forming apertures through, the sheet or wire; a sand blasting chamber for pitting the surface of the sheet or wire; or a mechanical punch for punching dimples into, or apertures through, the sheet or wire. All the foregoing texturizing devices are well known in the various arts of manufacturing and are not shown. The sheet or wire can have the texturizing feature placed on only one side or on both sides. In addition, the texturizing feature can be continuous or it may be intermixed with unmodified regions.

Figure 2:
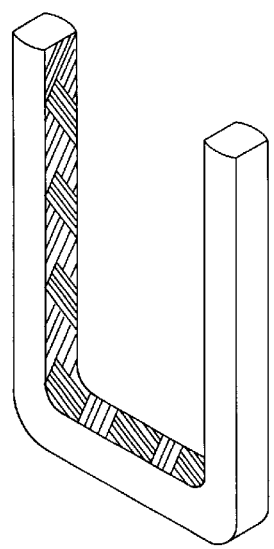
FIG. 2 is a perspective view of the fastener of FIG. 1 where the surface has been knurled with a cross-hatch design.
Figure 3:
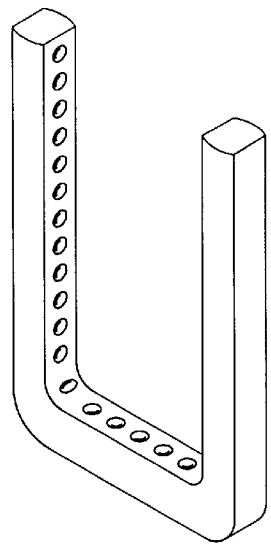
FIG. 3 is a perspective view of the fastener of FIG. 1 where the surface is dimpled.
Figure 4:
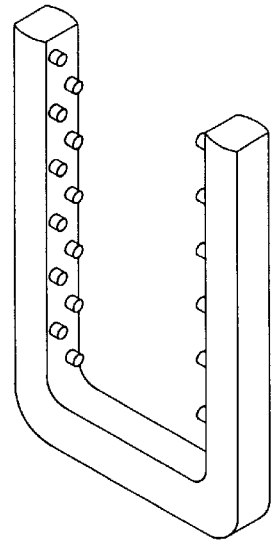
FIG. 4 is a perspective view of the fastener of FIG. 1 where the surface has protrusions.
Figure 5:
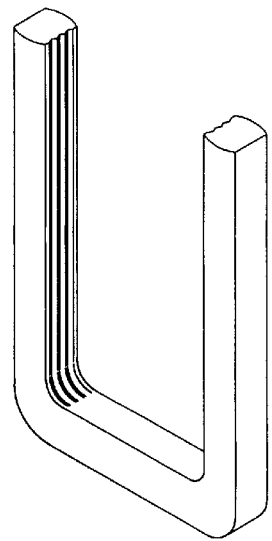
FIG. 5 is a perspective view of the fastener of FIG. 1 where the surface has linear grooves or flutes.
Figure 6:
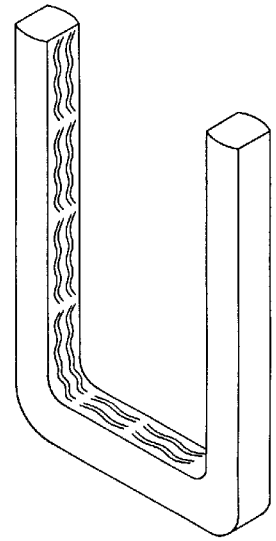
FIG. 6 is a perspective view of the fastener of FIG. 1 where the surface has curvilinear grooves or flutes.
Figure 7:
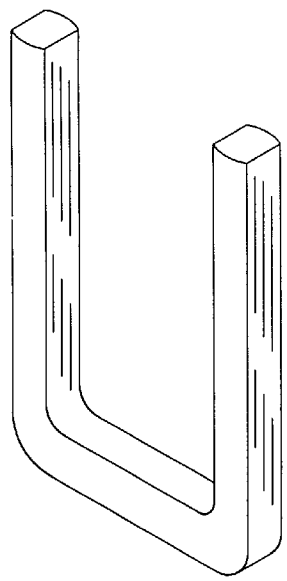
FIG. 7 is a perspective view of the fastener of FIG. 1 where the surface has been etched with a laser.
Figure 8:
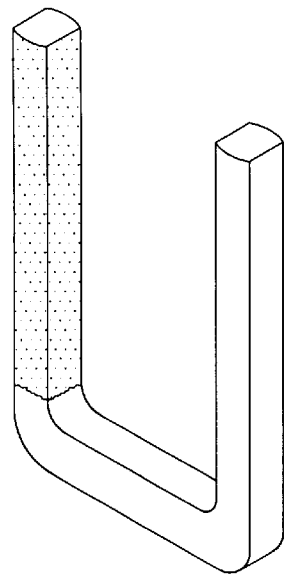
FIG. 8 is a perspective view of the fastener of FIG. 1 where the surface has been layered with an abrasive coating.
Figure 9:
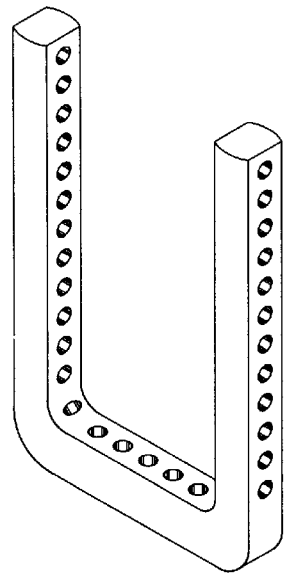
FIG. 9 is a perspective view of the fastener of FIG. 1 where the fastener has apertures therethrough.
Figure 10:
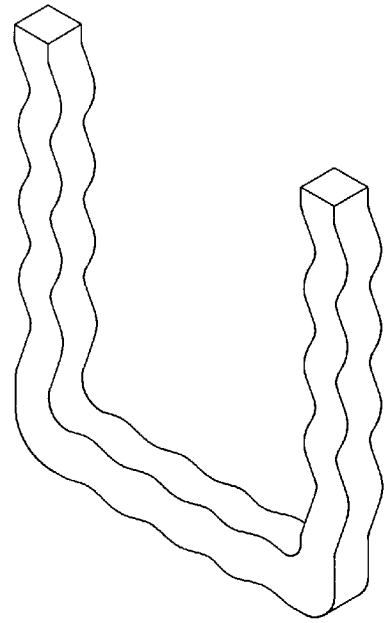
FIG. 10 is a perspective view of the fastener of FIG. 1 where the fastener has been crimped.
Figure 11:
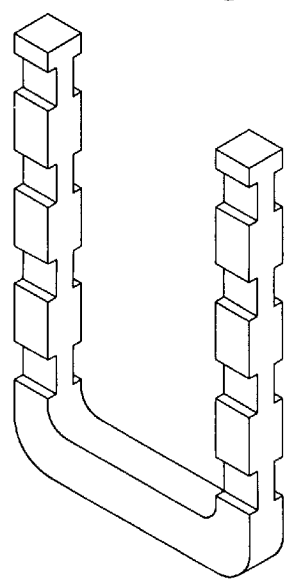
FIG. 11 is a perspective view of the fastener of FIG. 1 where the edges of the fastener have been notched.

Some illustrations of the texturizing features include a cross-hatch design as illustrated in FIG. 2, dimples as illustrated in FIG. 3, protrusions as illustrated in FIG. 4, linear grooves as illustrated in FIG. 5, curvilinear grooves as illustrated in FIG. 6, etchings from a laser as illustrated in FIG. 7, a layer of an abrasive coating as illustrated in FIG. 8, apertures from a mechanical punch or laser as illustrated in FIG. 9, crimping as illustrated in FIG. 10, or pitting from sand blasting as illustrated in FIGS. 19–22. In addition, the edges of the fasteners can have notches as illustrated in FIG. 11, which result from forming the dimples or apertures along a line where the individual fasteners will subsequently be separated. Some of the modifications are only effective to prevent slippage in one direction, such as the linear grooved surface of FIG. 5. The grooves of FIG. 5 are shown longitudinal along the fastener in order to prevent slippage of the fastener along the longitudinal of a blood vessel or the like, but could as easily be transverse along the fastener if another result was desired.

Figure 14:
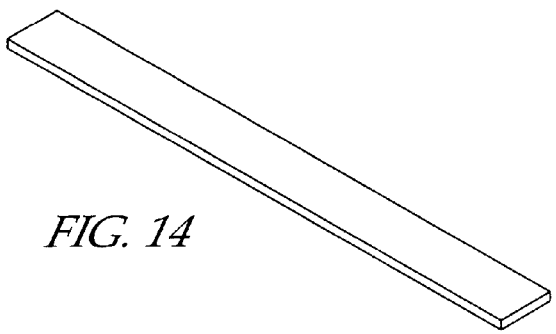
FIG. 14 is a perspective view of an alternate embodiment showing a linear shaped fastener before application.

After the texturizing feature has been added, the sheet or wire is pulled into a cutting device, typically comprising a die having a plurality of longitudinal and transverse knives if sheets are used. As the die is actuated into contact with the sheet, the longitudinal knives cut the sheet into a plurality of bands, usually between 0.20 to 0.35 inches, which is to become the length of the fasteners. Simultaneously, the transverse knives cut into, but not quite through, the sheet to form a plurality of fasteners, each fastener having a width usually between 0.015 to 0.030 inches. The individual fasteners are not separated from the band at this point but are not securely attached to each other and could be easily separated by hand. In the case of wire, the wire is cut into a plurality of members having a length usually between 0.20 to 0.35 inches, which is to become the length of the fasteners. The wire members are subsequently juxtaposed to form bands for further processing. If the embodiment of the fasteners is linear shaped as shown in FIG. 14, then the fasteners are packaged with a predetermined number of fasteners per package and distributed. However, if the fasteners are to be formed into the other embodiments shown in FIGS. 1, and 15–22, then the bands of fasteners are processed further.

After leaving the cutting device, the bands of fasteners are pulled into a press where an upper plate having a plurality of linear ridges presses the bands into a reciprocal lower plate having a plurality of linear grooves corresponding to the ridges in the upper plate. The number of ridges or grooves equals the number of bands so that each band is pressed into only one groove. The shape of the groove complements the shape of the ridge so that when a band of fasteners is pressed between the ridge and groove, the band of fasteners will take on the form of the ridge or groove, which corresponds to the embodiments shown in FIGS. 1, and 15–18. The fasteners are then packaged with a predetermined number of fasteners per package and distributed.

Figure 19:
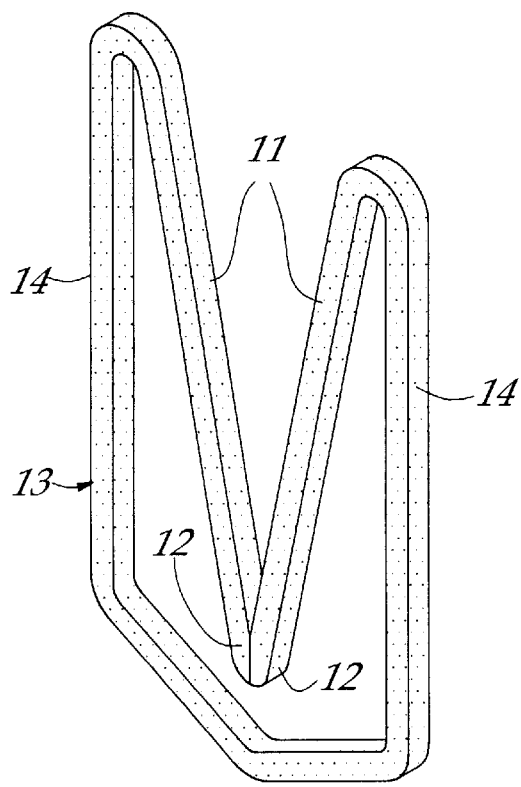
FIG. 19 is a perspective view of an alternate embodiment showing a double-walled fastener having an inner V-shaped portion before application.
Figure 20:
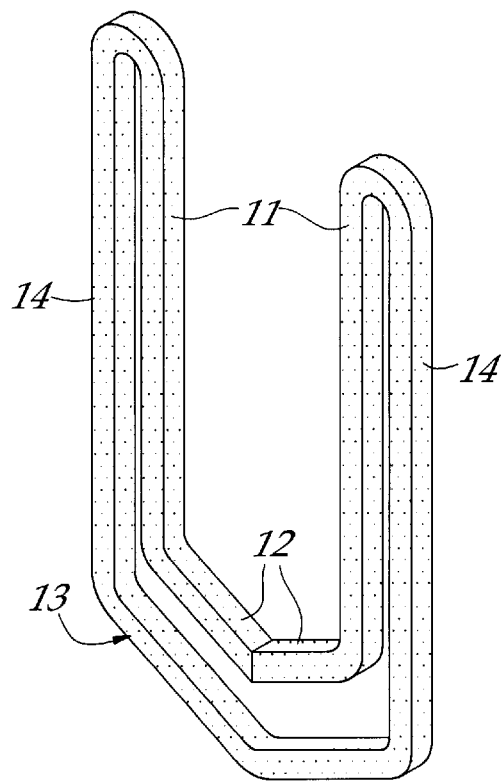
FIG. 20 is a perspective view of an alternate embodiment showing a double-walled fastener having an inner U-shaped portion before application.
Figure 21:
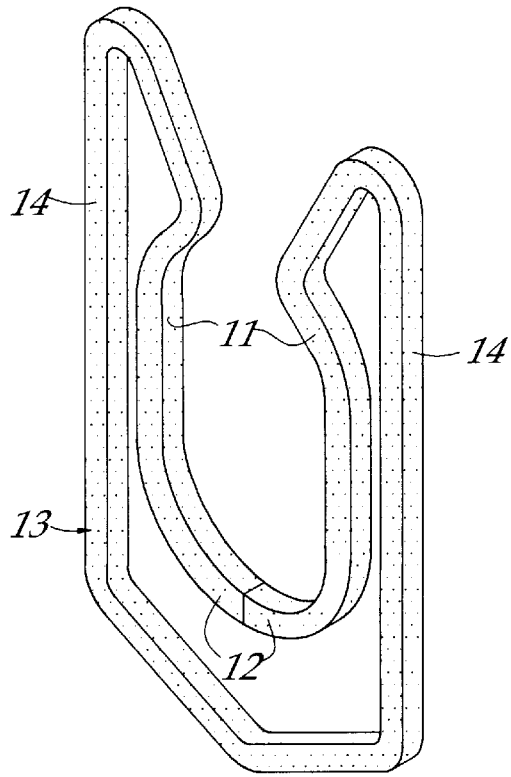
FIG. 21 is a perspective view of an alternate embodiment showing a double-walled fastener having an inner oval-shaped portion before application.
Figure 22:
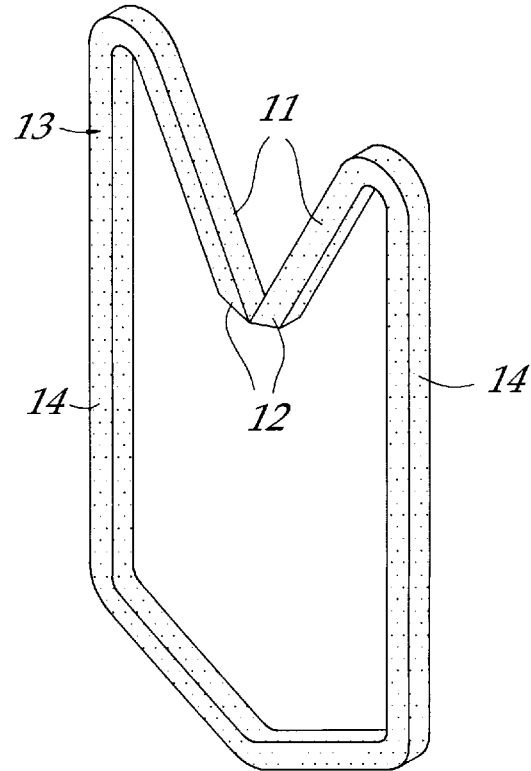
FIG. 22 is a perspective view of an alternate embodiment showing a double-walled fastener having an alternate inner V-shaped portion before application.

To make the embodiments illustrated in FIGS. 19–22, the fasteners are formed such that the bands are substantially wider (i.e., the length of the fastener) than the fasteners described hereinabove. After formation as described above, the distal ends of the elongated arms are folded back to form the inner wall 11 of the fastener. The distal ends are preferably folded in such a manner that the fastener ends 12 are in contact with each other. The outer wall 13 is preferably U-shaped, such that the outer portions 14 of the arms are parallel to each other, although this is not critical. The inner wall 11 of this embodiment can have various shapes, depending on the personal preference of the user as well as the procedures for which the fasteners are to be used. A fastener having an inner V-shaped wall is shown in FIG. 19; a fastener having an inner U-shaped wall is shown in FIG. 20; a fastener having an inner oval-shaped, or modified C-shaped, wall is shown in FIG. 21; and a fastener having an alternate inner V-shaped wall is shown in FIG. 22. It is to be understood that the fasteners of this embodiment are to be used in the surgical devices already existing. Accordingly, it may be seen that the addition of a secondary wall will diminish the space within the crimping or clamping device such that an additional mass of metal is compressed. By compressing the greater mass within the same volume a more certain seal is achieved. Note that the fastener walls are not merely thickened but formed in discrete segments to enhance the engagement about the vessel by selection of the particular inner configuration as shown.

Figure 12:
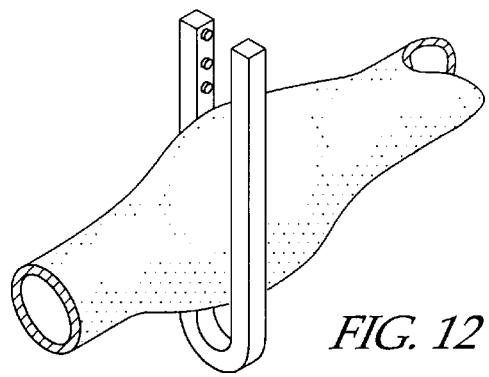
FIG. 12 is a perspective view of the fastener of FIG. 4 clamped around a blood vessel to prevent fluid transfer.
Figure 13:
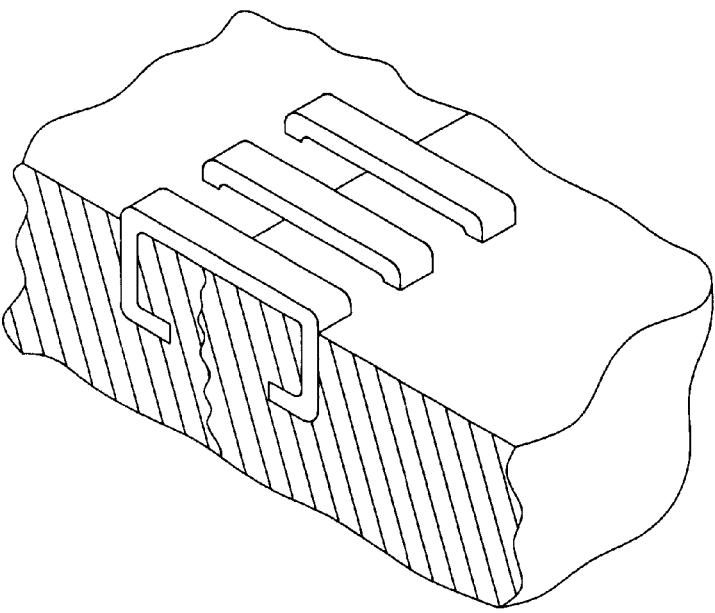
FIG. 13 is a perspective view of the fastener of FIG. 4 secured into tissue for maintaining closure of an incision.

The fasteners of the present invention can be used in surgical staplers utilizing anvils or in surgical applicators utilizing a vise. Application of surgical fasteners has been well documented in the prior art and will not be repeated here. A good example of the application of fasteners with an anvil type surgical stapler was discussed by Noiles et al. in U.S. Pat. No. 4,407,286. The present discussion will focus on the fastener during and after application into the tissue. As the fastener is secured to close incisions or wounds, or to clamp vessels or ducts to prevent fluid flow, the novel features of the present invention become apparent. As the fastener closes around tissue, the tissue forms about the texturizing features. Since the interface between the fastener and the tissue is not smooth, but rather rough and abrasive, the fastener will resist displacement arising from hydrostatic pressure, movement of adjacent tissues, or other occurrences which would tend to displace the fastener. A fastener embodying features of my invention is shown secured to a blood vessel in FIG. 12 and maintaining closure of an incision in FIG. 13. Furthermore, the embodiment comprising the double wall feature illustrated in FIGS. 19–22 has the added benefit of an outer wall 13 to promote uniform compression of the inner wall 11 during application of the fastener. During application of presently used fasteners, the resistance from tissue can deform the fasteners, such that there is not uniform closure. This can subsequently lead to displacement of the fastener and fluid loss or hemorrhage. The outer wall 13 of the present invention acts to bolster the inner wall 11 during application of the fastener so that the inner wall will compress properly over the tissue, and subsequently adds fortification to the inner wall to prevent deformation from increasing hydrostatic pressure in the tissue.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. A surgical fastener for use in a surgical applicator, said fastener comprising a textured feature to increase a gripping effect of said fastener, said textured feature comprising a biocompatible paint coating having a plurality of solid particles mixed therein such that said particles form protrusions in said coating after said coating has dried.

2. A surgical fastener for use in a surgical applicator, said fastener comprising an elongated member having a pair of legs wherein each of said legs is folded back on itself to form separate inner and outer contiguous segments, whereby tissue is received between said inner segments such that when said fastener is applied to the tissue with said applicator, each outer segment abuts its contiguous inner segment such that said inner segments are compressed into sealing engagement with the tissue and said outer segments provide reinforcement to said inner segments, wherein said fastener further comprises a textured feature to increase a gripping effect of said fastener, said textured feature comprising a coating containing a plurality of solid particles, wherein said particles form protrusions in said coating.

3. A surgical fastener comprising an outer segment of substantially U-shaped configuration having a pair of parallel legs and a pair of separate inner segments defined by extensions of said legs folded within said outer segment wherein said inner segments form a U-shape for receiving a vessel transversely therein, whereby the vessel is received between said inner segments such that when said fastener is applied to the vessel, said outer segment abuts said inner segments and compresses said inner segments into sealing engagement with the vessel and said outer segment provides reinforcement to said inner segments.

4. A surgical fastener comprising an outer segment of substantially U-shaped configuration having a pair of parallel legs and a pair of separate inner segments defined by extensions of said legs folded within said outer segment wherein said inner segments form a C-shape for receiving a vessel transversely therein, whereby the vessel is received between said inner segments such that when said fastener is applied to the vessel, said outer segment abuts said inner segments and compresses said inner segments into sealing engagement with the vessel and said outer segment provides reinforcement to said inner segments.

5. A surgical fastener comprising a base portion having two parallel legs extending therefrom, wherein a portion of each of said legs is folded back towards said base portion such that each of said legs comprises separate inner and outer portions wherein said inner portions form a U-shape for receiving a vessel transversely therein, whereby the vessel is received between said inner portions such that when said fastener is applied to the vessel, said outer portions abut said inner portions to compress said inner portions into sealing engagement with the vessel and said outer portions provide reinforcement to said inner portions.

6. A surgical fastener comprising a base portion having two parallel legs extending therefrom, wherein a portion of each of said legs is folded back towards said base portion such that each of said legs comprises separate inner and outer portions wherein said inner portions form a C-shape for receiving a vessel transversely therein, whereby the vessel is received between said inner portions such that when said fastener is applied to the vessel, said outer portions abut said inner portions to compress said inner portions into sealing engagement with the vessel and said outer portions provide reinforcement to said inner portions.

7. A method of forming a textured feature on a surface of a surgical fastener to increase a gripping effect thereof, comprising the steps of:

(a) applying a biocompatible paint coating having a plurality of solid particles mixed therein to the surface of said fastener; and (b) drying said coating such that said particles form protrusions in said coating.

* * * * *